United States Patent [19]

Rowley et al.

[11] Patent Number: 5,196,334

[45] Date of Patent: Mar. 23, 1993

[54] UROGENITAL SINUS DERIVED GROWTH INHIBITORY FACTOR

[75] Inventors: David R. Rowley; Donald J. Tindall, Sr., both of Houston, Tex.

[73] Assignee: Baylor College of Medicine, Houston, Tex.

[21] Appl. No.: 240,171

[22] Filed: Sep. 2, 1988

[51] Int. Cl.$^5$ ............... C07K 15/00; C12N 5/00
[52] U.S. Cl. ............... 435/240.2; 530/324; 530/339; 530/828; 514/2; 514/21
[58] Field of Search ............... 530/324, 339, 828; 514/2, 12, 21; 435/240.2

[56] References Cited

U.S. PATENT DOCUMENTS

| | | | |
|---|---|---|---|
| 1,163,538 | 12/1915 | Hieatzman et al. | 424/559 |
| 1,651,770 | 12/1927 | Hartmann | 424/559 |
| 1,690,932 | 11/1928 | Hartmann | 530/412 |
| 3,008,878 | 11/1961 | Keck | 530/412 |
| 3,409,605 | 7/1975 | Florini | 530/399 |
| 3,867,363 | 2/1975 | Hansen | 530/395 |
| 3,901,870 | 8/1975 | Haupt et al. | 530/392 |
| 4,108,849 | 8/1978 | Thomas | 530/395 |
| 4,510,131 | 4/1985 | Donahoe | 424/105 |
| 4,708,948 | 11/1987 | Iwata | 514/2 |

OTHER PUBLICATIONS

Baird, *J. Cell Biochem. Supp.* Vol. 0, No. 11, Part A, p. 50 (1987), Abst. No. A192.
Johnson, *Cancer Treatment Reviews*, 2, 1–31 (1975).
Dai & Gupta (1990) J. Biol. Chem. 265 (32): 19871.
Ijzermans & Marquet (1989) Immunobiol. 179:456.
Quelle & Wojchowski (1991) J. Biol. Chem. 266(1):609.
T. R. Ulich et al. (1991) Exp. Hematol. 19:29.
A. Kimchi et al. (1988) Science 240:196.
Harel et al., Journal of Cellular Physiology 119:101–106 (1984).
Hus et al., Prac. Natl. Acad. Sci. U.S.A. 81:2107–2111 (Apr. 1984).
Roberts et al., Prac. Natl. Acad. Sci. U.S.A. 82:119–123 (Jan. 1985).
Rowley et al., Cancer Research 47:2955–2960 (Jun. 1, 1987).
Sporn et al., Science 233:532–534 (1986).
Steck et al., The Journal of Cell Biology 92:523–523 (Feb. 1982).
Wang et al., TIBS: 24–26.
Wells et al., Journal of Cellular Physiology 117:148–154 (1983).
Konig, et al, Urological Research 15:145–149 (1987).

*Primary Examiner*—F. T. Moezie
*Attorney, Agent, or Firm*—Fulbright & Jaworski

[57] ABSTRACT

A process is provided for purifying Urogenital Sinus Derived Growth Inhibitory Factor (UGIF) from embryonic tissue which comprises chromatographing medium from cultures of embryonic tissue derived from the urogenital sinus by gel filtration chromatography. Further purification by reverse phase high pressure liquid chromatography is also demonstrated. The UGIF is obtained in 70-fold to 8000-fold purification over the conditioned medium. A UGIF composition of matter is also provided.

4 Claims, 8 Drawing Sheets

UROGENITAL SINUS DERIVED GROWTH INHIBITORY FACTOR

BACKGROUND OF THE INVENTION

1. Field of the Invention

The present invention relates to urogenital sinus derived growth inhibitory factor, methods for its purification and its use in the inhibition of tumor or tumor cell growth.

2. Description of the Prior Art

The morphogenesis and cytodifferentiation of many tissues during embryogenesis is a result of interactions between stroma and epithelium. It has been postulated that local humoral factors from stroma act to induce morphogenesis. The induction of epithelial phenotype by stroma has been studied in a variety of tissues, including mammary gland, eye, skin, stomach, lung and prostate. At least some of these inductive effects have been shown to be produced by diffusable factors produced by the stroma.

The fetal urogenital sinus differentiates into the mature prostate gland as a result of tissue-tissue interactions. Specifically, the mesenchyme (stroma) acts to induce the differentiated phenotype of the apposing epithelium. The induction of the epithelial differentiated state by the stroma has been shown by Cunha et al. (for reviews see Cell Differentiation 17:137-148, 1985). It has been shown that during a specific window of time (day 17-19 in the fetal rat and mouse), the stroma induces the epithelium to express the normal differentiated state. Additionally, heterotypical tissue-tissue recombinant studies have demonstrated that urogenital sinus stroma at this stage can induce both fetal and adult bladder epithelium to that of a prostate-type epithelium. While bladder epithelium cells do not normally possess androgen receptors or antigens specific for prostate tissue, the induced epithelium demonstrated not only the morphology of a normal prostate epithelium, but also expressed androgen receptors and prostate specific antigens. Epithelial cells from mice with Testicular Feminization Syndrome (Tfm) do not respond to androgen hormone. However, when such Tfm epithelium was incubated as heterotypical tissue-tissue recombinants with normal urogenital sinus stroma a normally differentiated, prostate-appearing epithelium was produced which responded to androgen stimulation. Such studies point to the potent nature of the inductive influence of the urogenital sinus stroma. Currently, although little is known regarding the mechanisms of stromal-epithelial interactions in the developing urogenital sinus, the existence of certain paracrine acting factors which regulate growth and differentiation of epithelium in a local environment has been postulated.

The prostate gland developed from the urogenital sinus during embryogenesis. The prostate epithelium is induced by the mesenchyme (stroma) of the urogenital sinus. In tissue recombination studies, fetal rat urogenital sinus has been shown to induce both fetal and adult normal bladder epithelial cells to express a prostate-specific phenotype.

Additionally, factors produced by normal tissues have been shown to regulate the growth and differentiation of neoplastic cells. Urogenital sinus tissue has been shown by the inventor to alter the phenotype of normal bladder epethelial and bladder carcinoma cells. Among the alterations caused by the urogenital sinus tissue was the inhibition of cell proliferation, the stimulation of protein secretion and alterations in cell morphology.

The characterization and purification of UGIF from urogenital sinus organ explants and derived fibroblastoid monolayers represents a major advancement in understanding the role of such factor(s) in urogenital sinus development.

Because of the great applicability of urogenital sinus derived inhibitory factor (UGIF) and the need to provide a substantially purified UGIF, there is a need for a method of purification for, and substantially purified fractions of this material.

SUMMARY OF THE INVENTION

It is therefore an object of the present invention to provide a substantially purified UGIF.

If it another object to the invention to provide compositions comprising UGIF bioactive fractions.

It is another object of the invention to provide a method of inhibiting the growth of tumors and tumor cells.

Yet another object of the invention is to provide improved methods of treating certain carcinomas.

It is a further object of the invention to provide improved methods and compositions for treating urogenital disorders.

These and other objects of the invention as will hereinafter become more readily apparent have been attained by providing:

A process for purifying biologically active UGIF from tissue which comprises:
  (a) incubating urogenital sinus tissue in an appropriate aqueous culture medium for a time sufficient to synthesize and secrete UGIF from said tissue into said medium,
  (b) dialyzing the medium obtained in step (a) and collecting said UGIF,
  (c) chromatographing said UGIF obtained from step (b) on a gel filtration column and collecting fractions containing biologically active UGIF,
  (d) chromatographing said UGIF obtained from step (c) with a high performance (pressure) liquid chromatography system using reverse phase column(s) and collecting fractions containing biologically active of UGIF.

Other objects of the invention have also been attained by providing:

A composition comprising UGIF derived from tissue having an activity of at least 1 as measured by the UGIF units assay, being substantially free of albumin and being about 70-8,000 fold enriched in UGIF activity over the conditioned medium which was the starting material for the purification.

Yet other objects of the invention have been attained by providing:

A composition comprising UGIF derived from tissue having an activity of at least 1 as measured by the UGIF units assay;
  being substantially free of albumin and of proteinaceous material having a molecular weight of 10,000-20,000 Daltons; and
  being about 70-8,000 fold enriched in UGIF activity over the conditional medium starting material.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 7 demonstrates the effects of UGIF on cell morphology; 7A represents control cultures, 7B and 7C represent cells exposed to UGIF.

FIG. 8 demonstrates a polyacrylamide gel electrophoretic profile of UGIF at different stages of purity; 8A represents initial starting material and 8B represents material eluted from HPLC.

DETAILED DESCRIPTION OF THE INVENTION

The present invention provides a process for the purification of UGIF from urogenital sinus tissue.

The materials prepared at different stages of the process of the present invention are all distinct embodiments of the present invention, and they can all be used for the treatment of tumors in animals. The materials are particularly useful for the treatment of carcinomas in animals.

The process of the invention comprises excising urogenital sinus tissue from the fetal animals and thereafter incubating said urogenital sinus in culture medium at physiological temperatures (25°-37° C., preferably 37° C.). The medium should contain amino acids, vitamins and isotonic salts. Examples of incubation medium include DMEM, Basal Media Eagle's, CMRL 1066 or MEM.

Conditioned medium from the organ explants is preferably collected each 48 hours, but is not limited to this collection schedule. Incubation of medium longer than 48 hours per sequential collection does not increase the units of assayable UGIF activity in the medium.

UGIF may be purified from any source, such as, conditioned medium by chromatographic procedures. Any procedures may be utilized known to those of skill in the art which are capable of isolating a protein having the characteristics of UGIF, i.e., a molecular weight of 10,000-20,000 Daltons, acid stability, stability at 80° C. for at least 10 minutes, and having the biological effects of inhibition of cell proliferation of cell lines NBT-II, Mv 1 Lu, A-549, Y-79, NRK and primary fibroblasts derived from fetal rat urogential sinus.

In one embodiment, UGIF may be purified from medium which has been "conditioned" by incubation with organ explants of fetal rat urogential sinus (conditioned medium, CM). The CM containing approximately 70 units of UGIF activity per mg protein may be subject directly to chromatographic separation of the UGIF.

Alternatively, the conditioned medium may be acidified to precipitate acid insoluable proteins prior to application of the soluable fraction to the chromatographic column. Preferably, the acidification is achieved by dialysis of the CM with acid for 24 hours at 4° C. Most preferably, the CM is dialized against 1M acetic acid.

The dialysis of the conditioned medium with acid, preferably 1M acetic acid, for 24 hours at 4° C. results in the presence of precipitated protein and soluble protein in the resulting dialyzed medium. Assayable UGIF activity is obtained and recovered in the soluble fraction.

The UGIF containing solution is further purified by chromatographic methods. Preferably, the UGIF is concentrated prior to application to a chromatographic column. This concentration step may be omitted. However, application of concentrated UGIF to the columns provides larger yields and better recovery of UGIF. The UGIF concentration may be accomplished by any means known to those of skill in the art such as lyophilization or ultrafiltration. Preferably, the UGIF preparation is concentrated by lyophilization to dryness.

The UGIF preparation is next subject to chromatographic purification. Preferably, the first chromatographic step is carried out after the material obtained from dialysis is lyophilized to dryness. The dried sample is resolubilized in acid conditions, preferably, but not limited, to 1M acetic acid. The UGIF preparation is next subject to chromatographic purification. Preferably, the UGIF sample is chromatographed on a gel filtration column and separated from other proteins on the basis of molecular weight and/or molecular shape and size. The preferable gel filtration medium is Bio-Gel P-200 (Bio Rad. Corp.), however any gel filtration matrix that separates proteins on the basis of size and/or shape could be used.

After this step, the eluted fractions are assayed for UGIF biological activity using a biological assay such as those below described. Fractions containing significant units of UGIF activity are pooled and lyophilized to dryness.

The resulting lyophilized material is resolubilized in a solution compatible with high performance liquid chromatographic reverse phase (HPLC) column. Alternatively, UGIF concentrated by any other means is put into an HPLC compatible solution. The preferable solubilizing solution is 1% trifluoroacetic acid, but other suitable solution will be known to those of skill in the art. Any solubilizing buffer which is compatible with HPLC is acceptable. The preferable reverse phase column is one with a C18 configuration, yet is not limited to such. Any matrix which separates proteins based on their hydrophobic nature is acceptable. The HPLC column may alternatively be selected from the group consisting of BioGel TSK columns which have phenyl group columns, $C_4$ columns such as Hi-Pore RP304, and $C_{18}$ columns such as Hi-Pore 318, Bio-sil ODS-10 and ODS-55 or any other equivalent column.

After loading onto the HPLC column, proteins including UGIF are differentially eluted with any solvent or solution suitable to reverse the binding of proteins to said column. The preferable solvent is a 30%-80% gradient of acetonitrile added to the column at a rate of 0.5% change per minute.

After this step, the eluted fractions are assayed for UGIF biological activity using a biological assay. Fractions containing UGIF activity are dried by exposure to heat. Exposure to 70°-90° C. for 10 minutes is suitable; alternatively the fractions are allowed to air dry.

This preparation can be stored at −20° C. for indefinite periods. The purification of UGIF by this procedure is indicated in Table I.

TABLE I

| Step | Purification of UGIF: | | | |
|---|---|---|---|---|
| | Protein (mg) | UGIF Units | Units/ Protein | Fold Purification |
| CM | 177 | 12400 | 70 | 1 |
| Dialyzed CM | 172 | 12400 | 72 | 1 |
| P-200 Peak | 2.4 | 11861 | 4942 | 70 |
| HPLC Peak | 0.015 | 8324 | 554933 | 7928 |

The data in Table I summarizes the results obtained from a starting volume of original urogenital organ explant conditioned medium of 50 ml.

It is fully anticipated that additional purification modifications will lead to the complete purification of UGIF to homogeneity.

Once the UGIF is sufficiently homogenous, the amino acid sequence can be determined.

In addition, the UGIF of the present invention can be used to develop polyclonal and monoclonal antibodies specific for UGIF, which can be used to develop immunoassays for UGIF. Such assays could be used clinically to assay for UGIF in human or animal tissues and/or fluids. Additionally, the UGIF antibodies can be utilized to further purify UGIF utilizing affinity techniques known to those of skill in the art. UGIF antibodies can also be used to neutralize UGIF biological activity should excess UGIF activity be associated with a disease state or otherwise abnormal condition.

Once the amino acid sequence is determined, oligonucleotides may be synthesized and the antibody probes and synthetic oligonucleotides used to clone the cDNA and genomic genes which code for UGIF. The clones will be used to genetically engineer microbiological organisms to produce UGIF. Such genetically engineered organisms will be used to produce large quantities of UGIF for clinical and/or research purposes.

The determination of UGIF biological activity in aliquots from each aforementioned step is determined by either or both of the following assays. The mink lung epithelial (Mv 1 Lu cell) miniassay utilizes the inhibition of tritiated thymidine incorporation into DNA effected by exposure of the cells to UGIF. For this assay, Mv 1 Lu cells are seeded in tissue culture wells ($6.0 \times 10^3$ cells/well of a 96 well dish) and exposed to samples of UGIF solubilized in the appropriate culture medium. After exposure of the cells to the UGIF for 20-22 hours, the Mv 1 Lu cells are exposed to tritiated thymidine (2 uCi/ml) for 2-3 hours. The cells are then fixed in an acid-methanol fixative (50% phosphate buffered saline, 37.5% methanol, and 12.5% acetic acid), washed with methanol followed by 5% TCA, followed by methanol, extracted with 200 ul of 1N NaOH, neutralized with the same volume of 1N HCl and radioactivity is determined by scintillation counting.

The second assay is the Y-79 cell suspension assay. The principles of this assay are identical to the miniassay described above with the exceptions that Y-79 cells are used instead of Mv 1 Lu cells. Y-79 cells, a human retinoblastoma cell line, grow in suspension rather than in monolayers. Accordingly, this assay requires one day less for completion. In addition, this assay precludes the potential interpretation that growth inhibition might be due to endogenous levels of transforming growth factor type beta (TGF-B), since Y-79 cells are negative for TGF-B receptors and do not respond to TGF-B. Y-79 cells seeded at $4 \times 10^4$ cells per ml/well in Bfs medium. The wells are exposed to UGIF active samples for 22 hours. Tritiated thymidine is added at 2 uCi/ml for 2-3 hours. The cells are collected from the tissue culture well, washed extensively with ethanol followed by 5% TCA on filters (AH-539,2.4 cm) in a sampling manifold, and the filters are scintillation counted for radioactivity. Although these assays are preferable, any bio-assay which distinguishes UGIF samples based on the ability to inhibit cell growth (nucleotide incorporation and/or cell number) is suitable for measuring UGIF biological activity. In addition, since UGIF acts to alter cell morphology and the secretion of newly synthesized proteins, any assay which would distinguish experimental samples based on these properties would be acceptable.

Figure 5:
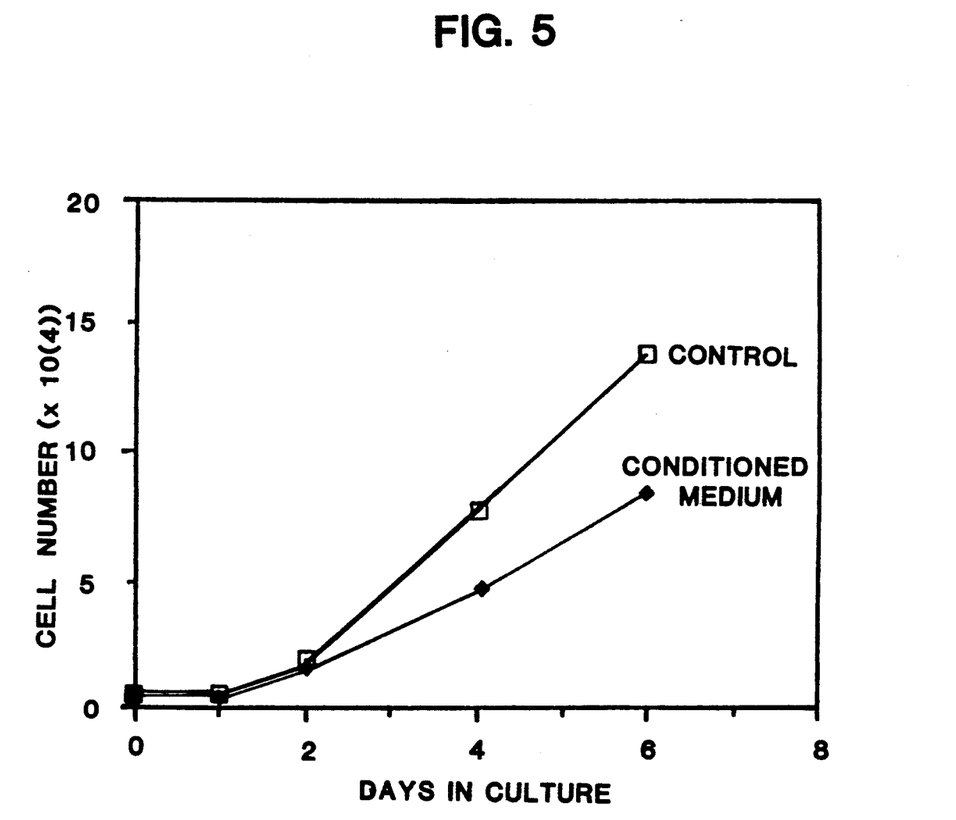
FIG. 5 demonstrates the inhibitory effects of UGIF on cell proliferation.

The purifed active UGIF-rich fractions of the present invention exhibit profound effects on the inhibition of growth or the selective destruction of transformed cells and tumors (FIG. 5). UGIF inhibits the growth of several cell lines of varied tissue origins and from at least three species of distant phenotypic and genotypic profiles. Table II demonstrates that UGIF inhibits normal and transformed cells and cell lines from rat bladder carcinoma (NBT-II), mink lung (Mv 1 Lu), rat urogenital sinus (normal fibroblasts), normal rat kidney (NRK), human lung carcinoma (A-549), human cervical carcinoma (HeLa), and human retinoblastoma (Y-79). Accordingly UGIF appears to affect a diverse and varied types of cells and/or tissues from several species.

TABLE II

| Cell lines inhibited by UGIF | | |
|---|---|---|
| Name: | Tissue Derived From: | Cell Type: |
| NBT-11 | Rat Bladder Carcinoma | Transitional Cell |
| Mv 1 Lu | Fetal Mink Lung | Epithelial |
| A-549 | Human Lung Carcinoma | Epithelial |
| Y-79 | Human Retinoblastoma | Retinoblastoma |
| HeLa | Human Cervix Carcinoma | Epithelial |
| NRK | Normal Rat Kidney | Fibroblast |
| UGS fibroblasts | Fetal Rat Urognital Sinus | Fibroblast |

*: All cell lines were inhibited by >50% (Thymidine incorporation assays) (30% volume/volume CM)

The active UGIF-rich fractions of the invention are administered to animal cells including human cells in tissue culture in an assay system to cells derived from either a rat carcinoma or human carcinoma and retinoblastoma.

Figure 4:
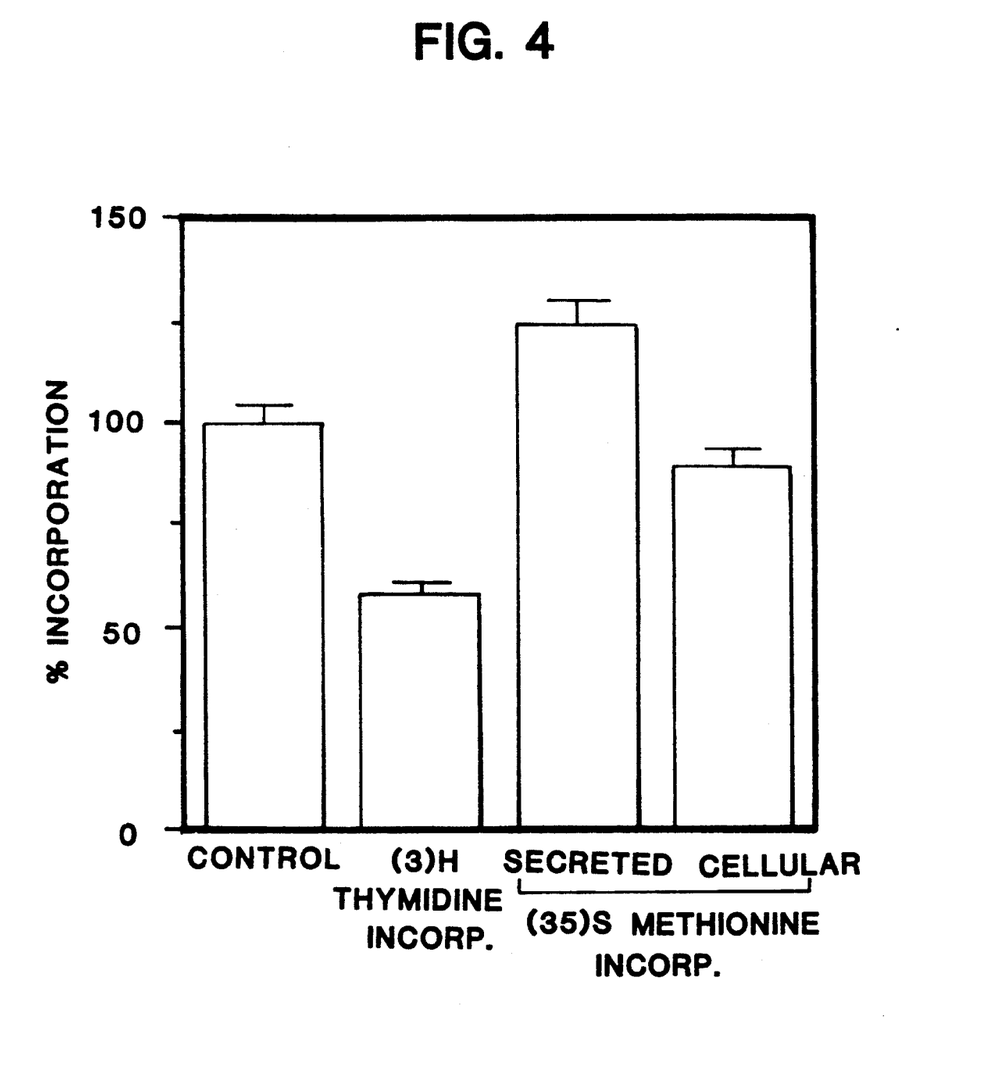
FIG. 4 demonstrates the stimulation of protein synthesis and secretion by UGIF.
Figure 6:
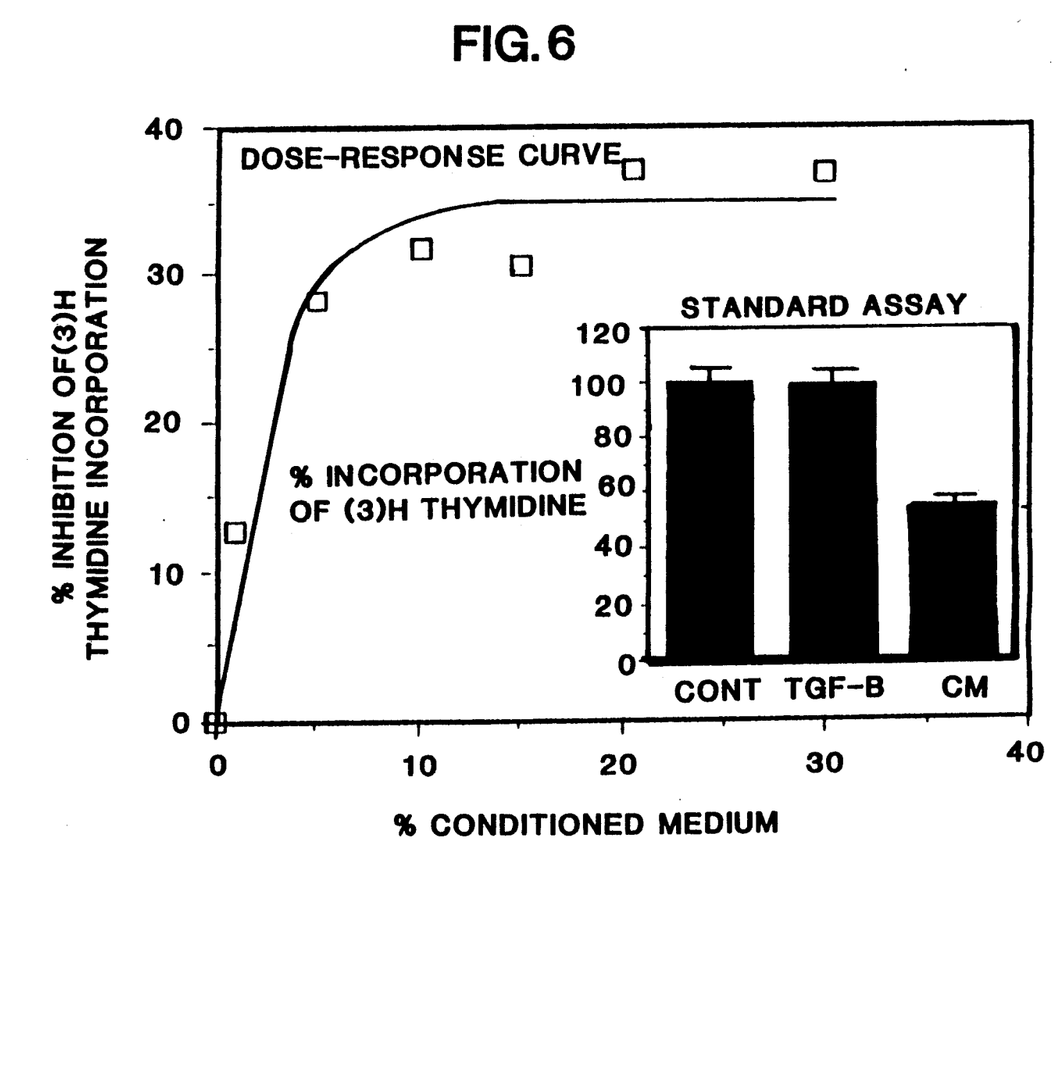
FIG. 6 demonstrates the dose-response effects of UGIF on the $Y^3H$ thymidine incorporation in Y-79 cells.
Figure 7A:
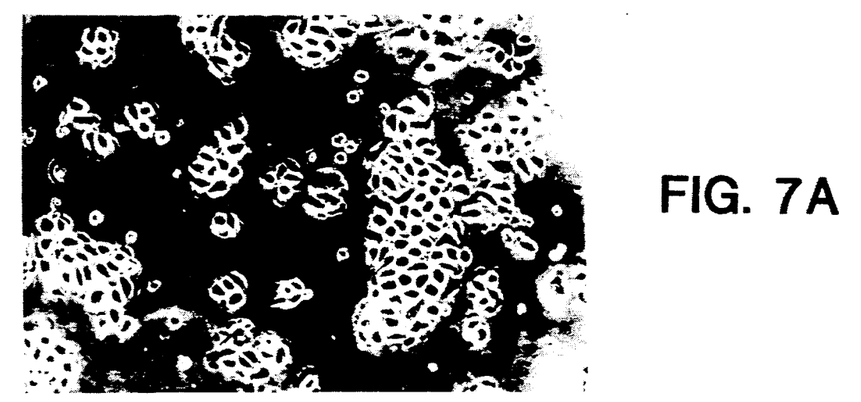
Figure 7B:
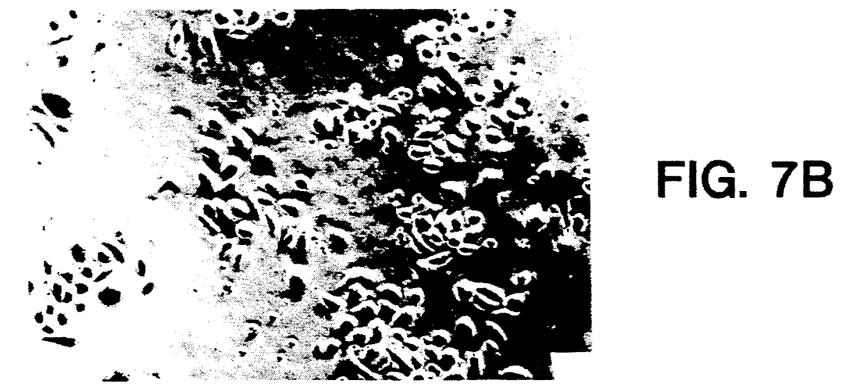
Figure 7C:
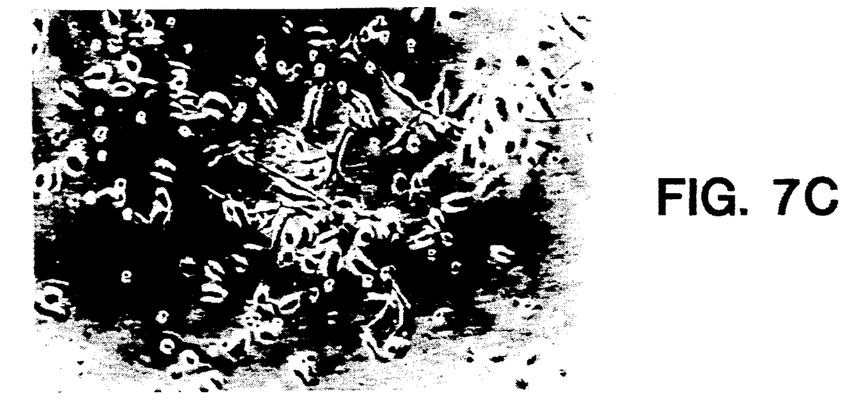

The active UGIF-rich fractions from each step of purification protocol of the present invention exhibit profound effects on the inhibition of growth of transformed cells (FIG. 4). The active UGIF-rich fractions of the invention are administered to a wide variety of animal and human cells in tissue culture at varying concentration levels. UGIF is active at low concentrations (pM levels) and cell cultures demonstrate a linear, dose-response curve to UGIF administration (FIG. 6). Cell cultures demonstrate a saturable response to increased concentrations of the UGIF of the present invention. In addition to altering cell growth, UGIF alters cell morphology and the secretion of proteins (FIGS. 7 and 4, respectively).

The units of UGIF biological activity are determined by analysis of data generated with the biological assay using cells in culture as described previously. For determination of UGIF units of activity, the following analysis of data is done. A standard linear curve of percent inhibition (relative to control cultures) versus percent conditioned medium added to the respective culture is generated. The conditioned medium (crude preparation) used to generate the standard curve is stored frozen in identical aliquots for use in one assay. Hence, each units assay is scored versus an identical standard curve. For the standard curve the percent conditioned medium (CM) value which produces a maximal inhibition of tritiated thymidine incorporation prior to or just at the point of saturable response to increased CM concentrations, is assigned a units score of 2. The negative control is assigned a units value of 0. The percent CM which generates one-half maximal inhibition is assigned a units value of 1. Accordingly, the experimental sample(s) being tested will produce a certain percent inhibition based on the concentration of UGIF present in the specific sample. This level of inhibition is scored versus the levels of the standard curve and a units score can be assigned to the experimental sample. Accordingly, for any specific sample to be tested, a units value of 0 through 2 will be determined. If a particular sample scores outside the sensitive range of 0-2, then an aliquot of greater volume (higher concentration of UGIF) or lower volume (lower concentration of UGIF) is reassayed from the same sample. The units of activity in the aliquot tested are then adjusted to determine the total units present in the entire sample.

UGIF shares several physiochemical and biological properties with other known growth regulatory factors. However, there are key properties of UGIF which differentiate UGIF from other known factors. The two most closely related factors are transforming growth factor type beta (TGF-B) and fibroblast growth regulatory factors (FGRs). The similarity between these factors lies in their ability to inhibit cell growth. Like UGIF, TGF-B is heat and acid stable, and has a molecular weight of about 25 kiloDaltons under non-reducing conditions. The Y-79 cell line used in the suspension assay to test for UGIF activity does not respond to TGF-B and does not contain TGF-B receptors. An additional distinction is shown by the fact that TGF-B stimulates the growth of the NRK cell line (Normal Rat Kidney Cells), whereas UGIF inhibits the growth of this cell line. These lines of evidence show clearly the distinct nature of UGIF as compared to TGF-B. UGIF is distinct from the FGR factors which are heat labile and have a molecular weight of 10-13 kiloDaltons; UGIF being heat stable and having molecular weight of 10-20 KiloDaltons. For these reasons, it is clear that UGIF is distinct as compared to the FGRs.

Since most transformed cells tested to date (murine and human) have shown response to UGIF, it is likely that the UGIF receptor is ubiquitous in nature and found on many eukaryotic cells. Moreover, UGIF is probably a highly conserved across species lines, since rat, mink and human cells respond in a highly similar manner. As is the case with most other growth factors, the ubiquitous nature of the receptors relates to the ubiquitous presence of the corresponding growth factor. Accordingly, it is likely that UGIF can be isolated from many types of eukaryotic tissues and/or cells. The production and isolation of UGIF is therefore not restricted to urogenital sinus tissue.

Similarly, UGIF has been shown to inhibit the growth of a wide variety of cell types from a number of different species. For this reason, administration of UGIF to an individual with any carcinoma or other neoplastic diseases will provide an effective treatment for these diseases.

Additionally, since UGIF causes the differentiation and diminished proliferation of normal cells, conditions related to hyperplasis of the urogenital sinus derived cells, such as the disease of benign prostatic hyperphasia (BPH), or prostatitis, or testicular feminization syndrome (Tfm), or any other disease or malady which affects the growth or differentiated state of the fetal, neonatal, or adult prostate gland or urogenital sinus derived tissues such as vagina and cervix in the female, will benefit from treatment with UGIF.

In addition to the treatment of cancer related tumors in humans as well as in animals, there exists a potential use of UGIF in the treatment of other clinical manifestations dealing with abnormalities of the genitourinary system. Diseases which are manifested by a loss, lack or change in the normal tissue or cell differentiation could be treated by UGIF since this factor induces changes in cellular phenotype (state of cell differentiation) to that more suggestive of the normal phenotype. Accordingly, UGIF could be used to treat Benign Prostatic Hyperplasia (BPH), and Prostatitis diseases in a high proportion of aging men. Moreover, UGIF could be used to treat certain fetal and neonatal diseases such as testicular Feminization Syndrome (Tfm), as well as other developmental abnormalities which produce an altered and otherwise abnormal tissue and/or cellular phenotype in any urogenital sinus derived tissues including the female vagina and cervix. It is clear and reasonable to suggest that any disease, syndrome, or otherwise irregularity of the genitourinary system could be affected by UGIF and could be induced to a state of more normal differentiation and phenotype.

Administration of the compounds useful in the method of the present invention may be by topical, parenteral, oral, intranasal, intravenous, intramuscular, subcutaneous, or any other suitable means. The dosage administered may be dependent upon the age, weight, kind of concurrent treatment, if any, and nature of the condition being treated. The effective compound useful in the method of the present invention may be employed in such forms as capsules, liquid solutions, suspensions, or elixirs, for oral administration, or sterile liquid forms such as solutions or suspensions. Any inert carrier is preferably used, such as saline, or phosphate-buffered saline, or any such carrier in which the compounds used in the method of the present invention have suitable solubility properties for use in the method of the present invention.

The term "individual" is meant to include any animal, preferably a mammal, and most preferably a cat, dog, cow or human.

The UGIF of the present invention including recombinant proteins and monoclonal antibodies thereto can be administered to an individual parenterally by injection, long release implants, rapid infusion, intravenously, nasopharyngeal absorption, dermal absorption, and orally. Preparations for parenteral administration include sterile or aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers for occlusive dressings can be used to increase skin permeability and enhance antigen absorption. Liquid dosage forms for oral administration may generally comprise a liposome solution containing the liquid dosage form. Suitable liquid dosage forms include emulsions, suspensions, solutions, syrups, and elixirs containing inert diluents commonly used in the art, such as purified water. Besides the inert diluents, such compositions can also include adjuvants, wetting agents, emulsifying and suspending agents, and sweetening, flavoring, and perfuming agents.

Generally, the dosage of UGIF protein administered to an animal will vary depending on such factors as age, condition, and whether alteration of cell/tissue differentiation or phenotype, or an inhibition of cell/tissue growth is the object of the administration, and other variables which can be readily ascertained and adjusted by one of ordinary skill in the art.

Having now generally described the invention, the same may be further understood by reference to the following examples, which are included herein for purposes of illustration only and are not intended to be limiting unless so expressly stated.

EXAMPLE 1

Assay of UGIF

Two procedures have been developed empirically to assay for UGIF activity. Both procedures are biological assays relying on the response of certain cells to UGIF as a score of activity.

A. Miniassay

This assay is referred to as the miniassay, since it is achieved with a minimum of cells in 96-well tissue culture microplates. The procedure was developed as a modification of the filter assay as published previously and was validated through comparison with the filter assay. This assay is compatible with any cell type which: (a) responds to UGIF with a decrease in tritiated thymidine incorporation and; (b) is anchorage dependent, that is a cell type which attaches to the culture plate (assay 1B is designed for cells grown in suspension).

Viable cells were seeded at a density of $6.0 \times 10^3$ cells/well in a 96 well tissue culture plate (Falcon), with 200 ul of growth medium/well, and allowed to attach and incubate for 24 hours in a tissue culture incubator at 37° C. and $5CO_2$. Growth medium for this assay was medium Bfs composed of 90% Dulbeccos modification of Eagle minimum essential media (DMEM), supplemented with 5% fetal calf serum, 5% Nu-Serum (Collaborative Research Inc.), penicillin (100 units/ml), streptomycin (100 ug/ml), insulin (5 ug/ml), and testosterone (0.5 ug/ml). Although medium Bfs is the preferred media, this assay is not restricted to this particular media. Any media which is compatible with the growth and viability of the chosen responding cell type would be acceptable. After the cells incubated for 24 hours, the media was removed and replaced with 200 ul of fresh media containing the sample to be assayed. For liquid samples, up to 30% v/v of the final volume can be tested. Dry samples (lyophilized) may be resolubilized directly in medium Bfs. Cultures were incubated for another 22 hours. After this incubation, 2 uCi/ml of $^3$H thymidine was added to each well, and cultures were allowed to incubate for an additional 2-3 hours. This incubation was stopped by the addition of a 50:50 mixture of phosphate buffer saline and methanol: acetate acid (3 parts methanol: 1 part acetic acid) for 5 minutes at room temperature. This step acts to chemically fix the cells to the culture surface and maintains the cellular structure. The cultures were then fixed further by the addition of full-strength methanol: acetic acid for 5 minutes at room temperature. The plates were then washed with 100% methanol (200 ul/well), followed by 5% trichloroacetic acid (TCA), (200 ul/well) for 5 minutes at room temperature. The cultures were then washed an additional 3 times with 100% methanol. The methanol wash steps act to wash out all the unincorporated, free thymidine (thymidine that has not been incorporated into DNA). The methanol primarily washes out the free thymidine from the cell cytoplasm. The TCA wash is primarily to wash the free thymidine from the cell nucleus. The cultures were then extracted with 1N NaOH (200 ul/well) for 5 minutes at room temperature. This step acts to hydrolyze all proteins and DNA to a soluble state in the NaOH. Aliquots (180 ul) were then removed from each well and added to scintillation vials which contained 180 ul of 1N HCl to neutralize the NaOH. This mixture was counted for radioactivity by scintillation counting. The cpm from the samples was then compared with those of the controls (wells not receiving UGIF preps.) and the % inhibition of tritiated thymidine incorporation relative to control was determined. The inhibition of ($^3$H) thymidine incorporation was approximately 50% under these conditions, identical to that shown in FIG. 4.

The assay to determine Units of UGIF bio-activity is the same as the miniassay just described. For the Units assay, crude conditioned medium from UGS organ explant cultures was used as a standard of UGIF activity. A large volume of crude conditioned media (CM) was saved frozen in 1 ml aliquots For each Units assay one of these identical aliquots was thawed and used as standard control. The standard CM was added to triplicate wells of cells in increasing concentrations (0–30% v/v). Previous studies have shown that with increasing concentration of CM, there was a linear correlation between % volume of CM and the % inhibition of thymidine incorporation. In addition, the response to CM was saturable, that is, above 15–20% CM the % inhibition was maximal and did not increase with increased concentration of CM. These properties were used to construct a method of analysis leading to the determination of Units of UGIF activity. The % CM value which gave 100% maximal inhibition was assigned a value of 2 Units. The % CM value which gave 50% maximal inhibition was assigned a value of 1 Unit, and 0% CM which gave 0% inhibition was assigned a Units value of 0. Each experimental sample was assigned a Units value based on a linear regression line of % inhibition versus Units as generated from the standard CM data. Therefore, the % inhibition of the unknown experimental was analyzed in the calculation and the Units for that specific sample was determined. All samples were compared on the same standard line plot.

The use of miniassay because of its accuracy, speed, and ease of use, has allowed for the assay of several hundred samples daily in the same assay. Accordingly, this assay has allowed for the analysis of the elution profiles from the P-200 column and the HPLC column with relative ease. Such a method of assay did not exist prior to the development of the miniassay described herein.

B. Suspension Assay

This assay is referred to as the suspension assay since it is designed to use cells which grow in suspension, that is cells which do not attach to the cell culture vessel surface. The preferred cell type is the Y-79 cell line (human retinoblastoma). However, this assay is not restricted to this cell type. Any cell type which (a) responds to UGIF by a decrease in cell growth and (b)

grows in culture in a suspension mode, i.e., does not attach to the cell surface.

The cells were seeded at a density of $4 \times 10^4$ cells/ml/well of a 24 well tissue culture vessel (Falcon). Preferable growth medium is Medium Bfs, however, any medium which supports the growth of the cell line used would be acceptable. At the same time of seeding the experimental samples were added at the appropriate levels to the seeding growth medium. The cells were allowed to incubate for 22 hours in a tissue culture incubator at 37° C. and 5% $CO_2$. [3]H Thymidine was added (2 uCi/ml) and cultures were allowed to incubate for another 2-3 hours. The incubation was stopped by the removal of media containing cells from individual wells and the addition of these cells to a Millipore filter manifold fitted with 2.4 cm glass fiber filters (934-AH, Whatman). The filters were then washed with 2 changes of ice cold ethanol (2 ml/well each wash), followed by 1 wash of ice cold TCA (1 ml/well), followed by 3 washes of ice cold ethanol (2 ml/well each wash). Each filter was removed from the manifold and added to a scintillation vial containing liquid counting scintillant. Cpm were determined by scintillation counting.

The suspension assay has allowed us to assay cells grown only in suspension such as the Y-79 cell line. This cell line has been valuable since it does not contain receptor for TGF-B growth factor. Accordingly, our data show that UGIF does not act through the TGF-B receptor system, at least with respect to the Y-79 cell line.

Both the miniassay and the suspension assay has allowed for the identification of UGIF in small aliquots and minialiquots simultaneously. These assays have allowed for the determination of UGIF in each step of the purification procedure described herein in the next example.

EXAMPLE 2

Purification of UGIF

Urogenital sinus (UGS) was removed intact from day 18 fetal rats. The UGS were placed in individual wells (1 UGS per well) of 96 well tissue culture dishes (Linbro) in 300 ul of media Bfs and allowed to incubate for 48 hour segments. Each 48 hours the conditioned medium (CM) from each well was collected and frozen at −20° C. until used. Previous studies have shown that there was no loss of UGIF activity after CM freezethaw as compared to freshly collected CM. Organ cultures of UGS were maintained for several months in the 96 well dishes. Also used were the monolayer of cells which emanated from the perifery of the UGS explants. These cells appeared homogeneous and were fibroblastoid in appearance. These cells were identified as fibroblasts based on morphological appearance. Upon sub-passage, the fibroblast cells attained confluence approximately 1 week after passage. Through this point UGIF was not produced (or secreted into the growth medium) by the cultures. After approximately 3-4 weeks in culture the fibroblast monolayers produced multicellular sphereoids which grew up from the monolayer of cells. At this point UGIF activity was produced by the spheroids (inferred from the data). Accordingly, CM media was collected each 48 hours from both the original UGS organ cultures and the spheroid cultures derived from the fibroblast monolayers. Studies have shown that approximately the same Units of UGIF activity (10-20 Units/ml) is produced by both UGS explants and spheroids, and that there are no differences in UGIF properties derived from either source. Hence, CM from both sources were stored and used separately for the purification procedure described herein.

Figure 1:
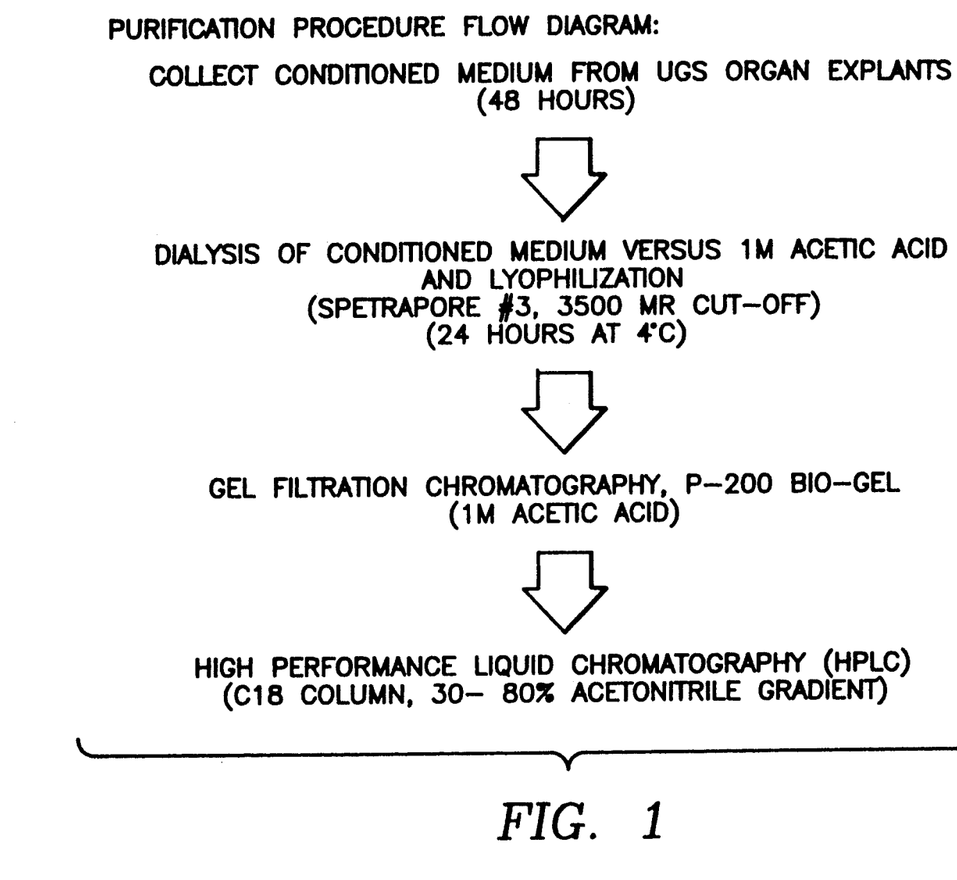
FIG. 1 shows the sequential steps in the purification of urogenital sinus derived factor.
Figure 2:
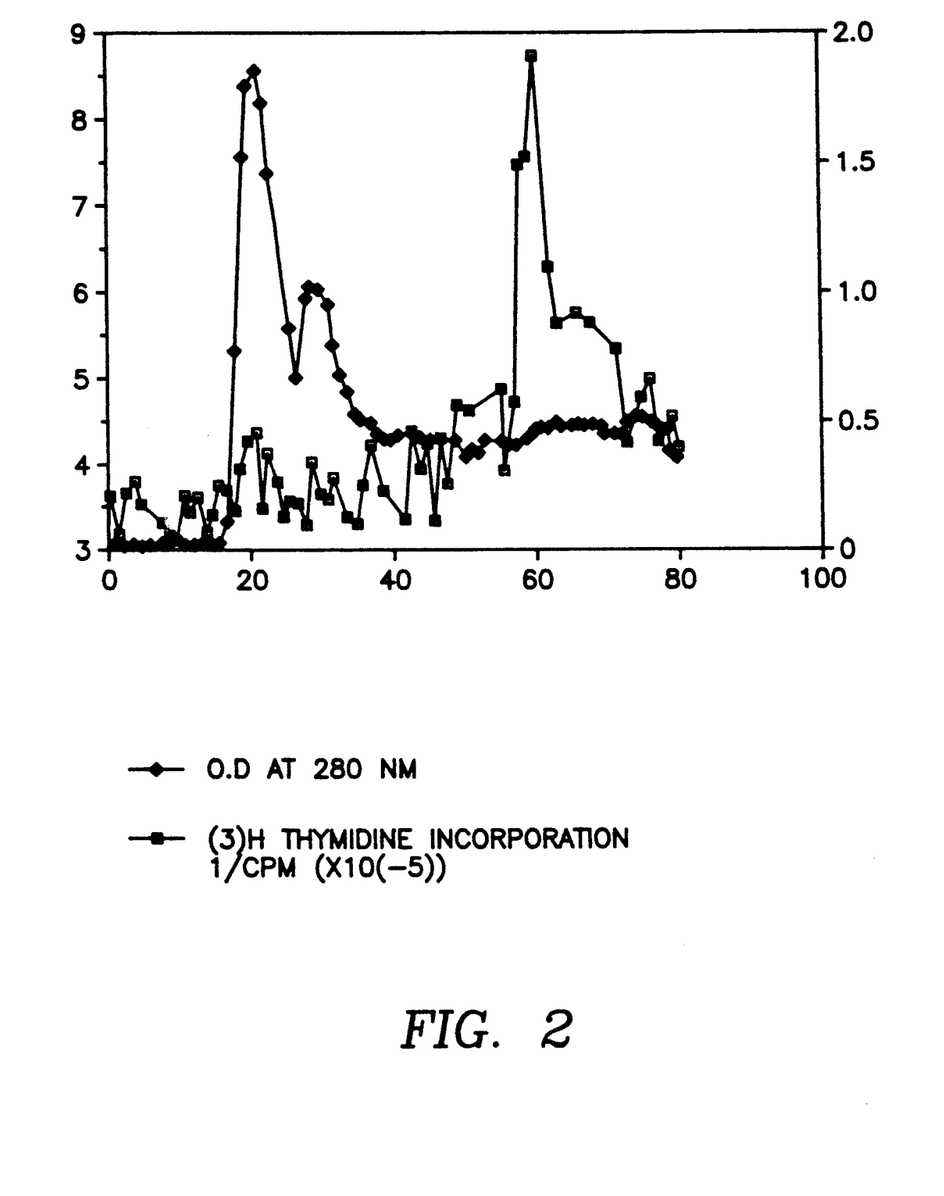
FIG. 2 demonstrates the elution profile of UGIF on a Bio-Gel P-200 column chromatography.
Figure 3:
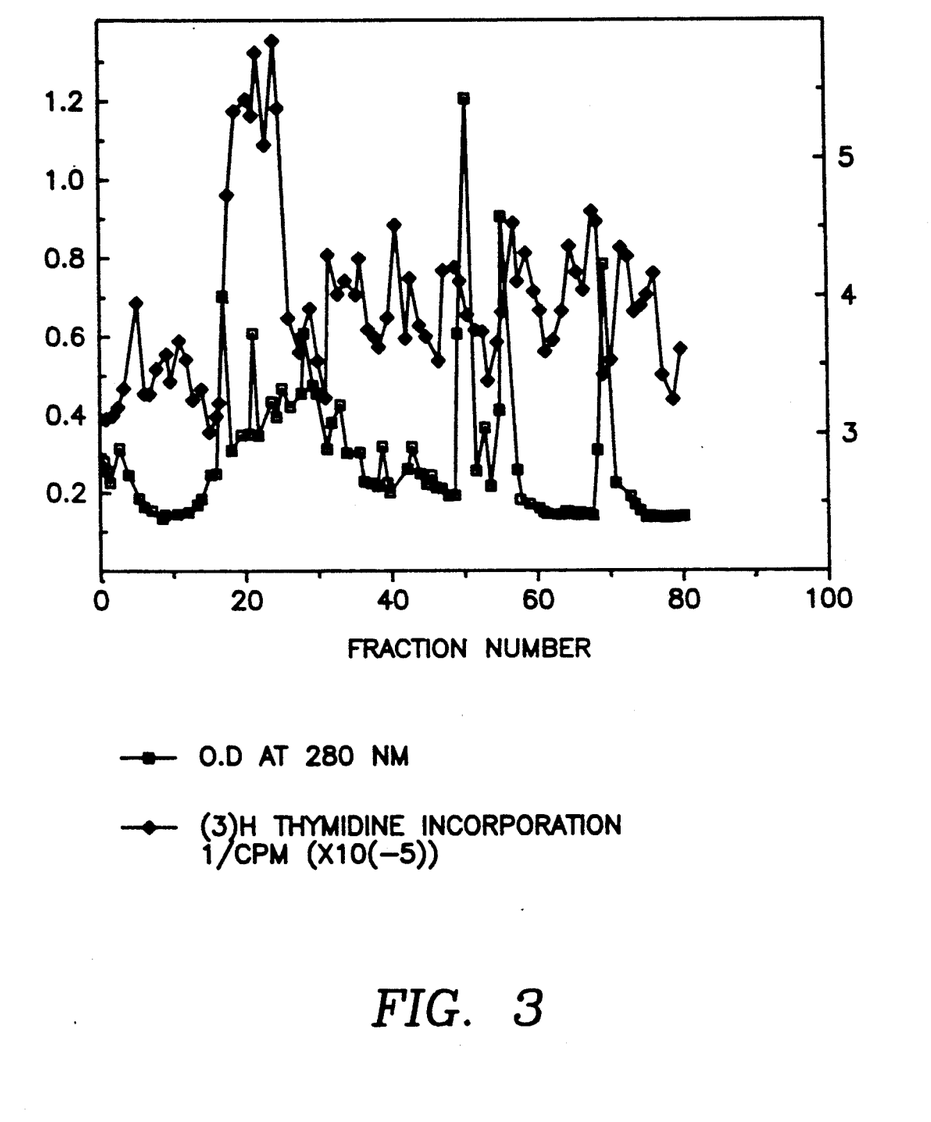
FIG. 3 demonstrates the elution profile of UGIF on a high performance liquid chromatography reverse phase column.

CM (150 ml) was next processed by dialysis versus 1M acetic acid (4 liters) for 24 hours at 4° C. using a Spectrapore dialysis bag (Mr cutoff at 3500). The preferred acid is 1M acetic yet any acid which does not lower the pH to less than 2.8 would be acceptable for this step and any step using 1M acetic acid hereafter. The purpose of dialysis versus acid was to place UGIF in a state of solubility such that hydrophobic interactions with gel matricies or containers was minimized. The dialyzed CM was next centrifuged to remove precipitated protein and the soluble fraction (50 ml batches) were lyophilized to dryness. The lyophilized material (equivalent to 50 ml CM) was resolubilized in 1M acetic acid (3 ml) for 24 hours at 37° C. This material of 3 ml volume was added entotal to a $66 \times 3$ cm column containing Bio-Gel P-200 beads (Bio-Rad), equilibrated in 1M acetic acid. Although P-200 is the preferred resin, any gel filtration matrix which withstands acid conditions, such as any of the Sephacryl (Pharmacia) matrix, would be usable. The column was eluted under a hydrostatic pressure of 75 cm $H_2O$ and 3.75 ml fractions were collected. Each of 80 fractions were assayed (100 ul/fraction) for UGIF activity using the miniassay as described herein. FIG. 2 demonstrates a typical elution profile of UGIF off the P-200 column. The peak of UGIF activity was pooled (Fractions #60-65) and lyophilized to dryness. The lyophilized material was resolubilized in 1% Trifluoroacetic acid (2 ml) and injected into a Beckman high performance liquid chromatography system fitted with a C18 reverse phase column and equilibrated in 30% acetonitrile. The column was eluted with a 30%-80% gradient of acetonitrile which elutes proteins retained by virtue of their hydrophobic properties. The column was eluted at 0.5%/ml/minute. Aliquots (100 ul) were assayed from each fraction using the miniassay as described herein. FIG. 3 demonstrates a typical elution profile of UGIF off the HPLC reverse phase C18 column. The fractions containing UGIF were pooled (6 ml total volume) (fractions #18-24) and represented an approximate purification of 8000-fold. FIG. 1 demonstrates the flow diagram of one embodiment of the purification procedure and see Table II for the purification values of a typical preparation. The final yield of UGIF was a 67% recovery which represents approximately 30 ug of UGIF based on current estimates of molecular weight and starting concentrations in crude CM. The pooled fractions were lyophilized to dryness and stored at −20° C. until use, or for indefinite periods.

Figure 8A:
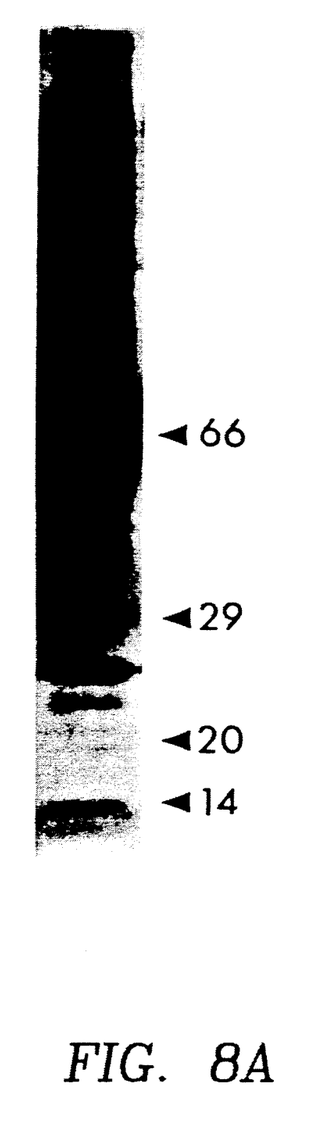
Figure 8B:
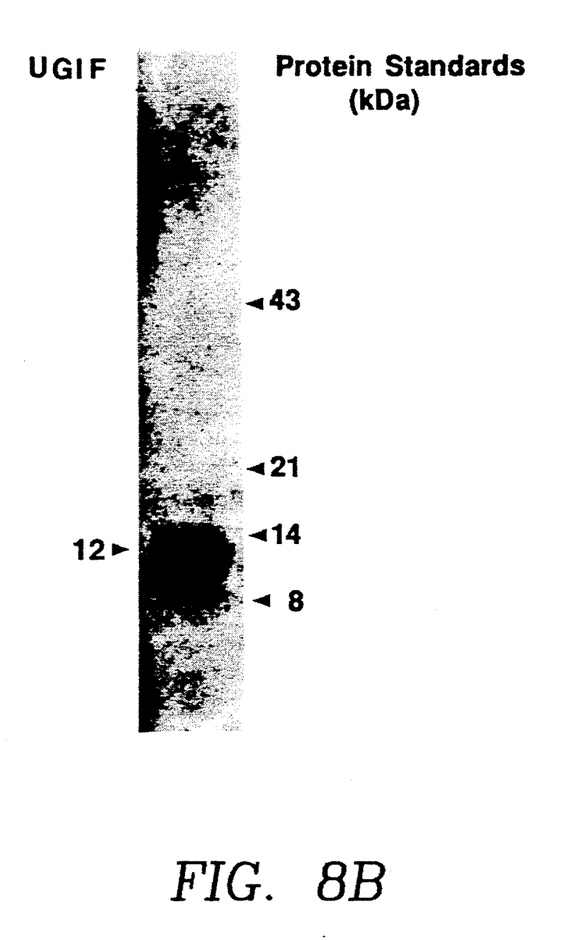

Aliquots were taken from each step of the purification procedure. Samples were prepared by lyophilization and resolubilized in Lammeli sample buffer (100 ul) without reducing agent. Samples were loaded onto 15% acrylamide gels and electrophoresed for 6 hours at 40-70 mAmp current. The gel was fixed in acetic acid methanol and subsequently stained in Coomassi Brilliant Blue. FIG. 8 demonstrates the photographic representation of the polyacrylamide gel electrophoresis of the UGIF. Lane 1 represents the starting material. Lane 2 represents the material eluted off the P-200 column and Lane 3 is off the HPLC column.

EXAMPLE 3

Inhibition of Neoplastic cell growth by UGIF

NBT-II cells were seeded at a density of $5 \times 10^4$ viable cells per cm$^2$ in 24 well tissue culture plates in the presence or absence of 30% volume/volume ratio of UGS conditioned medium. At days 1, 2, 4, and 6 after plating, the cell number per well was counted with an improved Neubauer hemocytometer. For counting the cells were harvested by brief exposure to trypsin (2.5%) and EDTA (0.25%). The cell number/well in the control and experimental was determined and graphed for each time point. The cells responded by a change in cell number by day 2–4 and by day 6 represented a different (inhibition of cell number by UGIF) of approximately 46% as demonstrated in FIG. 5. The alteration in cell number correlates well (but lags in time approximately by 48 hours) with the change in thymidine incorporation as can be seen and compared between FIGS. 5 and 4, respectively.

EXAMPLE 4

Inhibition of proliferation of Urogenital Sinus Fibroblast by UGIF

Primary cultures of fibroblasts (fibroblastoid appearing) cells were established from the monolayer of cells emanating from the perifery of the UGS organ explants. The organ explants were removed physically, and the primary fibroblasts were harvested by mild trypsinization (2.5%). The fibroblasts were seeded at a density of $5 \times 10^4$ cells/cm$^2$ in 24 well dishes. The cells were exposed to CM (30%) and control medium. The cultures were analyzed for incorporation of tritiated thymidine incorporation in a fashion identical to that described for the miniassay described previously. The thymidine incorporation was inhibited by approximately 50% when these cells were exposed to CM (containing UGIF bioactivity). See Table II.

EXAMPLE 5

Alteration in cell phenotype by UGIF

NBT-II cells were plated as those described in Example 3. The cells were exposed to CM (30% for 24 hours and certain wells contained 10 uCi/ml of [$^{35}$S] methionine. Control and experimental wells were photographed and then extracted with a buffer including sodium dodecyl sulfate and urea. The growth medium was saved and proteins were precipitated from it with exposure to 10% TCA, 4° C. for one hour. The precipitated proteins were harvested by filtration on glass-fiber filters, the filters washed extensively with ETOH and then scintillation counted. The cell monolayer extract was prepared and analyzed in an identical fashion. As shown in FIG. 4, when cells were exposed to UGIF, the secretion of newly synthesized proteins was increased by approximately 20%. In addition, the cells assumed a morphology not typical of epithelial cells. As shown in FIG. 7, the cells exposed to UGIF demonstrated filopodia and lamellipodia (cellular extensions) and were more spread out in their appearance as compared to the typical epithelioid appearance of the control cultures. These results show that not only does UGIF affect the growth rate of cells, it also affects phenotypic properties of cells, i.e., the differentiated state of cells.

Having now fully described this invention, it will be appreciated by those skilled in the art that the same can be performed within a wide range of equivalent parameters of composition, conditions and modes of administration without departing from the spirit or scope of the invention or of any embodiment thereof.

What is claimed is:

1. Substantially pure polypeptide urogenital sinus derived growth factor, UGIF, having the property of inhibiting the growth of Y-79, A-549, Mv-1 Lu, NRK, NBT-II, and Hela cells, further having the properties of:

(a) a molecular weight of 10 to 20 kiloDaltons;
   (b) being stable at 80° C. when exposed for 10 minutes; and
   (c) acid stability.

2. The substantially pure polypeptide urogenital sinus derived growth factor of claim 1 further characterized as having an activity of at least 1 as measured by the UGIF units assay test; being substantially free of albumin and of proteinaceous material, being 70–8000 fold enriched in UGIF activity over natural tissue per dry weight of said tissue.

3. The substantially pure polypeptide urogenital sinus derived growth factor of claim 1 having a specific activity greater than 70 units per mg protein as measured by the UGIF units assay test.

4. An in vitro method of inhibiting the growth of cells containing UGIF receptors which comprises contacting said cells with a growth suppressing amount of said UGIF composition of any of claim 2, 3 or 1.

* * * * *

UNITED STATES PATENT AND TRADEMARK OFFICE
CERTIFICATE OF CORRECTION

PATENT NO. : 5,196,334
DATED : March 23, 1993
INVENTOR(S) : David R. Rowley

It is certified that error appears in the above-indentified patent and that said Letters Patent is hereby corrected as shown below:

Column 1, line 5, between the Title and field of Invention, add--
The invnetion was made with Government support and the Government has certain rights in the invention--.

Signed and Sealed this

Twenty-seventh Day of August, 1996

Attest:

BRUCE LEHMAN

Attesting Officer

Commissioner of Patents and Trademarks